United States Patent
Nag

Patent Number: 6,027,443
Date of Patent: Feb. 22, 2000

[54] APPARATUS AND METHOD FOR HUMAN ARTIFICIAL INSEMINATION AND EMBRYO TRANSPLANTING

[75] Inventor: Kamala M. Nag, 88 Howard St., #1703, San Francisco, Calif. 94105

[73] Assignee: Kamala M. Nag, San Francisco, Calif.

[21] Appl. No.: 09/089,069

[22] Filed: Jun. 2, 1998

Related U.S. Application Data

[63] Continuation-in-part of application No. 08/789,419, Jan. 29, 1997, abandoned.

[51] Int. Cl.[7] .................................................. A61B 17/43
[52] U.S. Cl. ............................................................ 600/33
[58] Field of Search ........................ 600/33–35; 604/27, 604/43, 45, 117, 264, 275, 278, 279, 280, 55

[56] References Cited

U.S. PATENT DOCUMENTS

| | | | |
|---|---|---|---|
| 4,642,094 | 2/1987 | North, Jr. et al. | 600/34 |
| 4,790,814 | 12/1988 | Fischl et al. | 600/35 |
| 5,147,315 | 9/1992 | Weber | 600/35 X |
| 5,360,389 | 11/1994 | Chenette | 600/34 |

FOREIGN PATENT DOCUMENTS

| | | | |
|---|---|---|---|
| 8200754 | 3/1982 | WIPO | 600/34 |

*Primary Examiner*—Samuel Gilbert
*Attorney, Agent, or Firm*—Bruce H. Johnsonbaugh

[57] ABSTRACT

An apparatus and method for human artificial insemination and embryo transplanting are provided wherein a catheter is utilized having an extremely flexible barrel which has sufficient flexibility and softness to avoid irritation or trauma of the walls of the cervix and uterus. The catheter is made of high elasticity polyvinyl chloride and is more than ten times as flexible as prior art catheters. The method includes positioning the female recipient in a flat, supine position with pelvis elevated and legs flexed. The cervical canal, internal os and the lower segment of the uterine cavity are expanded with a speculum to minimize the distance from the vaginal opening to the uterine cavity and to minimize contact between the barrel of the catheter and the cervical and uterine walls. The soft and extremely flexible barrel of the catheter is inserted through the vaginal opening, through the cervical opening and into the uterine cavity and introducing either semen or an embryo into the uterine cavity.

4 Claims, 5 Drawing Sheets

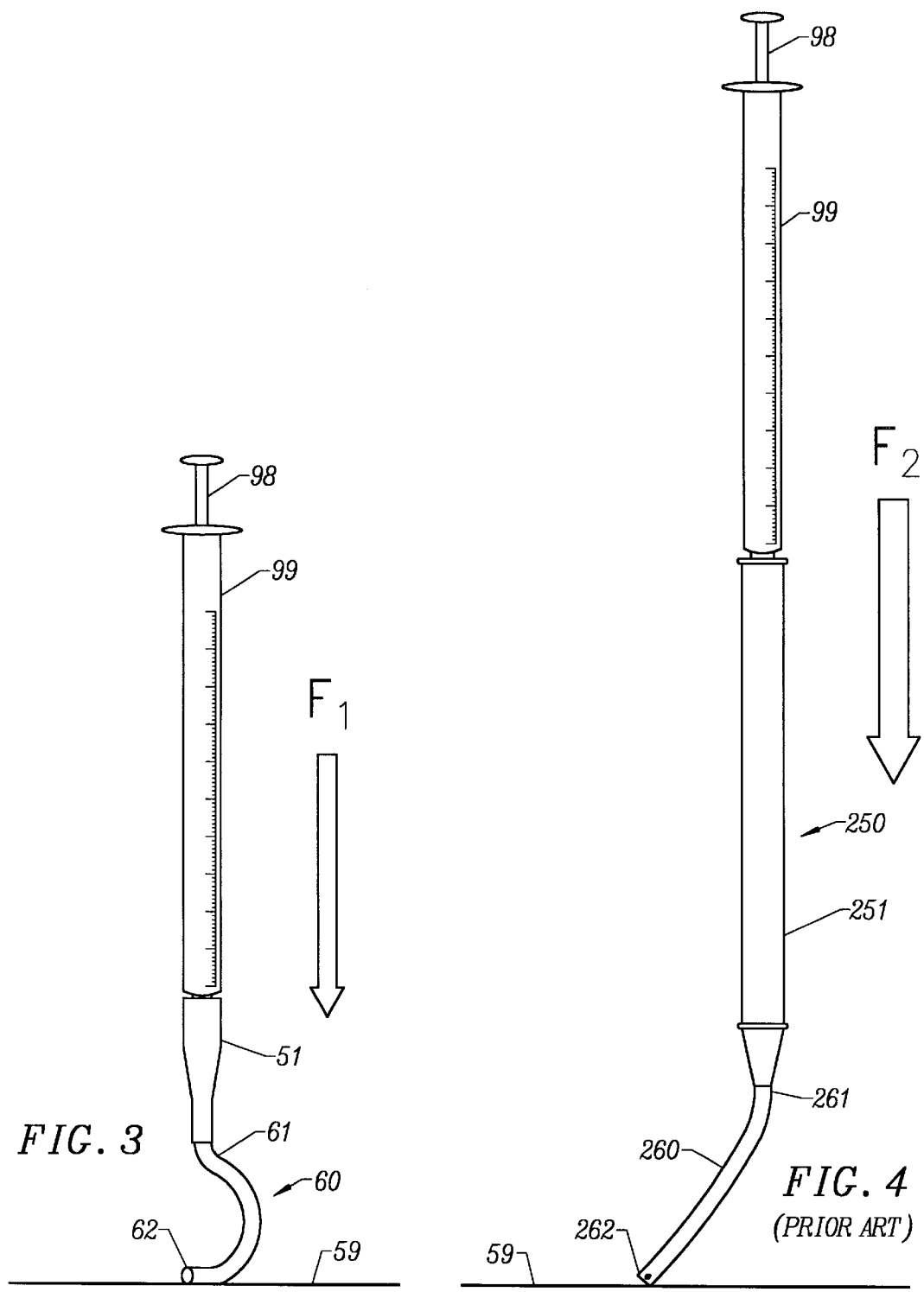

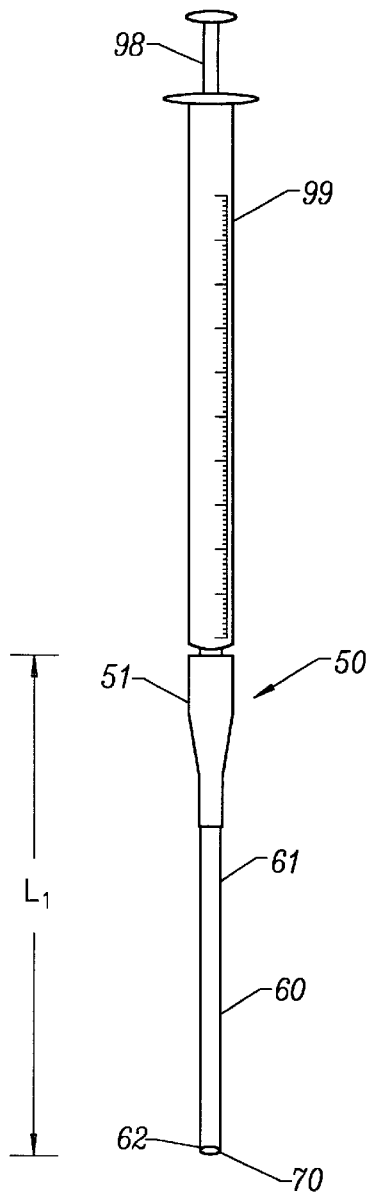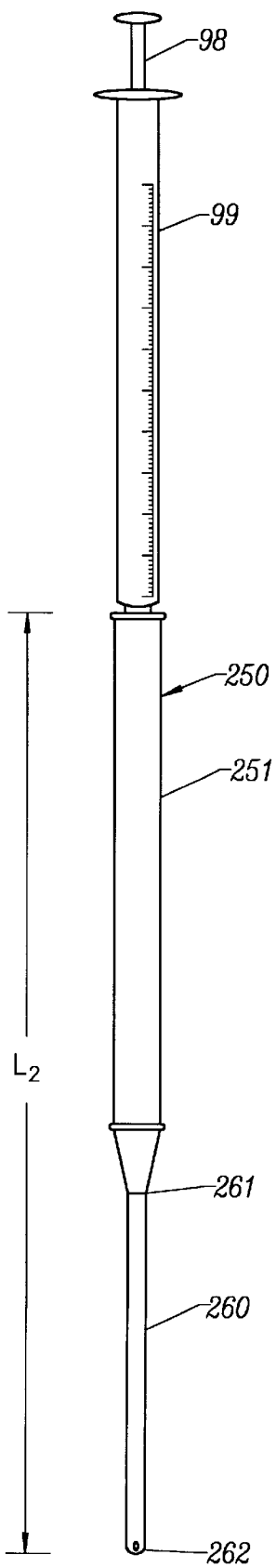
FIG. 5
FIG. 6
(PRIOR ART)

APPARATUS AND METHOD FOR HUMAN ARTIFICIAL INSEMINATION AND EMBRYO TRANSPLANTING

CROSS REFERENCE TO RELATED APPLICATION

This application is a continuation-in-part of application Ser. No. 08/789,419 filed Jan. 29, 1997, now abandoned.

BACKGROUND AND BRIEF SUMMARY OF THE INVENTION

This invention relates generally to the field of human fertility. More particularly, the invention relates to an apparatus and method for increasing the success rate in either human artificial insemination or embryo transplanting.

The prior art includes several catheters for use in either artificial insemination or embryo transplanting. Such catheters are typically metallic or relatively stiff elastic. The use of relatively stiff catheters can easily result in a traumatic insertion and cause irritation of the walls of the cervix or uterus. Such irritation brings about the unwanted response of the uterus expelling the transferred sperm or embryo and a failed fertilization effort. In fact, the following observation was made by Aby Lewin et al in a recent article entitled "The Role of Uterine Straightening by Passive Bladder Distension Before Embryo Transfer in IVF Cycles" (incorporated herein by reference) published in *Journal of Assisted Reproduction and Genetics*, Vol. 14, No. 1 (1997), at page 33:

> "A traumatic insertion of the ET [embryo transfer] catheter has long been recognized as a cause of endometrial bleeding and uterine contractions, possibly responsible for the expulsion of embryos from the uterine cavity. * * *"

The technique most frequently used in the prior art is placing the patient in the lithotomy position and grasping the anterior lip of the cervix with a tenaculum and pulling downwardly to straighten the utero-cervical angle in order to introduce a relatively stiff catheter into tile cervix and through the internal os to reach the uterine cavity. The effect of utilizing this position and grasping and pulling the anterior lip of the cervix downwardly results in narrowing and elongation of the uterine cavity, the internal os, and cervical canal. In attempting to negotiate the extra distance and the narrowed passage with a relatively stiff catheter, the chances of causing irritation and/or possible trauma of the walls of the cervix or uterus are quite high, which creates the risk of expulsion of the semen or embryo.

Another serious drawback of prior art catheters is trauma caused by their relative stiffness, as reflected by the force necessary to cause them to bend or to buckle. Such force is provided by the walls of the cervix or uterus and stiffer catheters inherently cause greater trauma. The present invention reduces the force necessary to bend the catheter by 95% as compared to the catheter shown in the Fischl et al U.S. Pat. No. 4,790,814.

The apparatus and method of the present invention minimizes and, in some instances, eliminates the irritation and possible trauma of the walls of the cervix and uterus. According to the present invention, the patient is placed in a position to minimize the distance between the vaginal opening and the uterine cavity, i.e., the patient is placed in a supine position on a flat surface with her pelvis elevated and legs flexed with feet apart. The cervical canal is dilated with a bivalved speculum introduced into the vagina and encircling the cervix. The speculum is opened, causing dilation of the cervical canal and the internal os, and separation of the anterior and posterior walls of the lower segment of the uterine cavity.

According to the present invention, an extremely flexible catheter is utilized. The flexible, soft catheter bends easily if it contacts the wall of either the cervix or uterus, minimizing and possibly eliminating irritation or trauma. The catheter of the present invention bends and buckles in response to a force of only 0.1 ounce. Because of the dilation of the cervical canal, internal os and lower segment of the uterine cavity, the catheter reaches the uterine cavity with little or no contact with the cervical or uterine walls.

The positioning of the patient according to the present invention minimizes the distance between the vaginal opening and the uterine cavity, thereby allowing the uses of a catheter with minimum length, which tends to minimize the contact with and irritation of the cervical or uterine walls.

In addition, due to non-traumatic transfer, it may avoid risk of subsequent added problems due to development of uterine abnormalities.

A primary object of the invention is to provide an apparatus and method for use in human artificial insemination and embryo transplanting which minimizes irritation and/or trauma of the uterine and cervical walls, thereby enhancing the success rate of the fertility procedure.

Another object of the invention is to provide a catheter for use in either human artificial insemination or embryo transplanting which is extremely flexible and which avoids, or at least minimizes, contact with and irritation of the cervical and uterine walls.

A further object of the invention is to provide a method of human artificial insemination and embryo transplanting which minimizes irritation of the uterus and cervical walls and increases the success rate of fertility procedures.

Another object of the invention is to provide a method of human artificial insemination and human embryo transplanting which maximizes the comfort of the patient and which minimizes trauma to the uterine and cervical walls, thereby increasing the fertility success rate.

Other objects and advantages of the invention will become apparent from the following description and the drawings wherein:

BRIEF DESCRIPTIONS OF THE DRAWINGS

FIG. 3 is a schematic representation of the relatively small force $F_1$ necessary to cause the catheter of the present invention to bend and to buckle;

Figure 7:
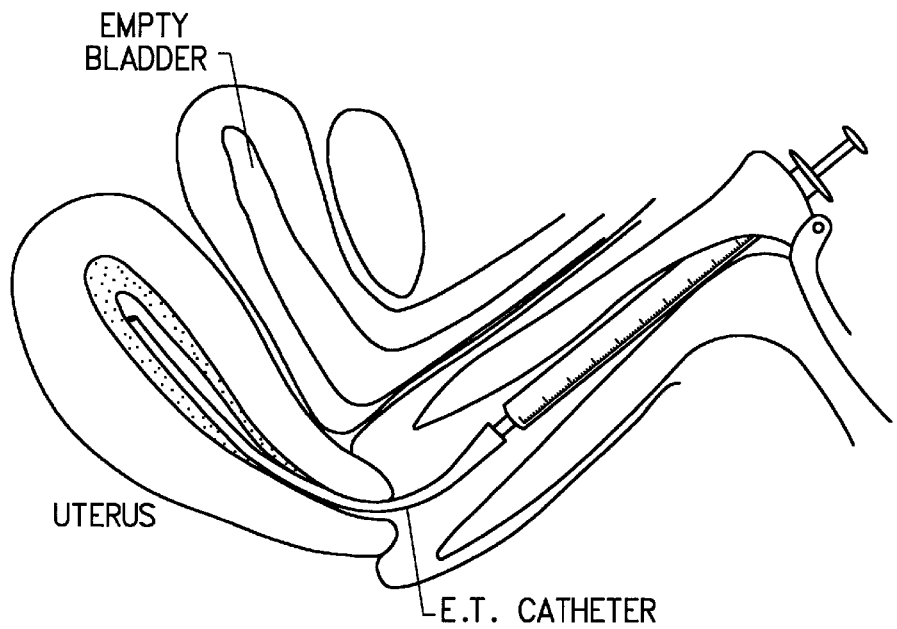
Figure 8:
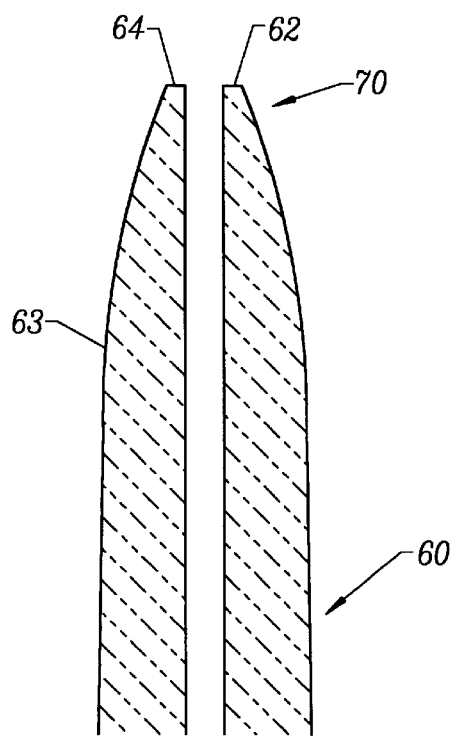

FIG. 4 is a schematic representation showing the relatively large force $F_2$ necessary to cause bending of the prior art Fischl et al catheter shown in U.S. Pat. No. 4,790,814;

FIG. 5 is a schematic representation of the catheter of the present invention as mounted on a standard syringe;

FIG. 6 is a schematic representation of the Fischl et al prior art catheter mounted on a standard syringe;

FIG. 7 is a schematic representation of a prior art ET catheter being utilized in conjunction with a speculum; and FIG. 8 is a schematic representation of the tip of the catheter.

DETAILED DESCRIPTION OF THE DRAWINGS

Figure 1:
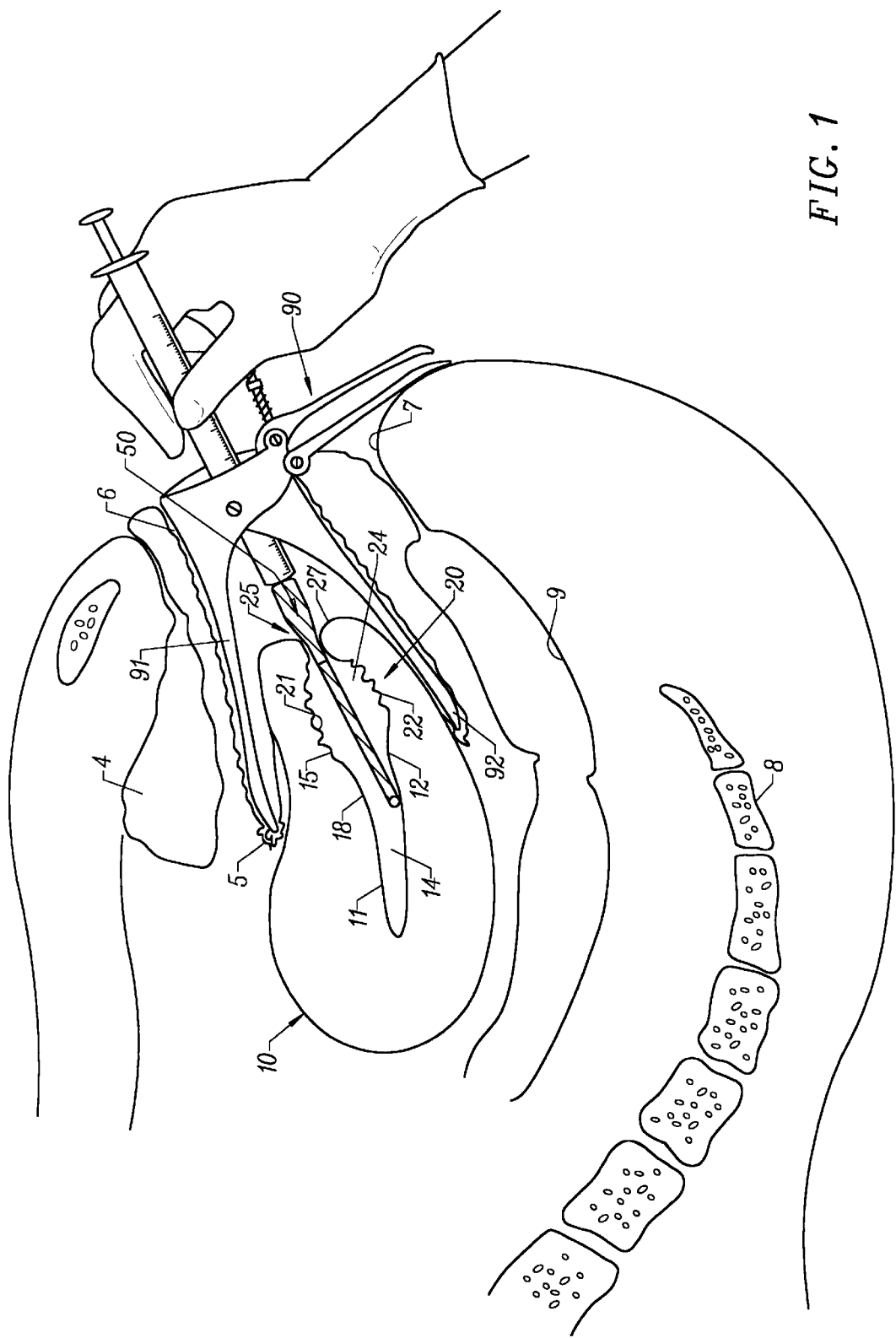
FIG. 1 is a schematic representation of the vagina, uterus and cervical opening, a speculum and the catheter of the present invention wherein the extremely flexible catheter is utilized together with positioning of the patient's body to minimize the distance between the vaginal opening and the uterine cavity.

FIG. 1 shows schematically the relative positioning of the uterus and cervix when using the method and apparatus of the present invention. The female recipient is lying flat in a supine position with her pelvis rotated and elevated approximately 45° and legs flexed or bent so that the knees are bent approximately 90° and the feet are spaced approximately three feet apart. The patient is lying on a flat surface with only her pelvis rotated and elevated. The uterus is shown generally as 10 and has uterine walls 11 and 12 and a uterine cavity 14 between the walls 11 and 12. The cervix is referred to generally as 20 having crypts 21 and 22 forming cervical cavity 24. The cervical opening 25 is formed at the lower end of the cervix.

For reference, the patient's rectum 9 is shown and the base of the spine 8 is also shown. The patient's anus is shown as 7. The vaginal walls are shown as 6; the tissue and ligaments supporting the uterus within the abdomen are shown as 5 and the patient's bladder as 4.

In this position, a speculum 90 is introduced into the vaginal opening, is extended around the cervix and is pushed high up to its full length and then opened to cause dilation of the cervical cavity 24 by separation of the cervical walls 21 and 22. In this position, the cervical canal, the internal os 15 and the lower segment 18 of the uterine cavity are dilated to form the widest possible passageway for the catheter. Also in this position, the distance between the anterior lip 27 of the cervix and the uterine cavity 14 is minimized, as is the distance between the vaginal opening and the uterine cavity 14. By minimizing the distance through which the catheter must pass and by maximizing the distance between the cervical walls 21 and 22 and dilation of the internal os 15, the pathways which must be traversed by the catheter, is minimized in length and maximized in width, with the overall purpose of minimizing or eliminating frictional contact between the catheter and the walls of the cervix and uterus. Upper blade 91 and lower blade 92 of speculum 90 are shown in FIG. 1. Speculum 90 is pushed upwardly and outwardly to reduce the utero-cervical angle, that angle being the angle between the longitudinal axes of the uterus and cervix. By way of contrast, FIG. 7 shows the typical angular pathway that prior art catheters typically negotiate to enter the uterus, the angle between syringe and the distal tip of the prior art catheter being approximately 70° as shown in FIG. 7. FIG. 7 is reproduced from the same article by Aby Lewin et al, referred to at page 1 above. In the present invention, the angle negotiated by the catheter is essentially zero degrees.

The new catheter according to the present invention is shown generally as 50 (FIG. 5) and includes a base 51, a flexible barrel means 60 and a tip means 70. The flexible barrel means 60 has proximal and distal ends 61 and 62, respectively. The barrel means 60 is preferably made of high elasticity polyvinyl chloride ("PVC") tubing or fluorinated ethylene polypropylene ("FEP"). It is preferably sterilized in boiling water for approximately thirty minutes, removed from the boiling water, dried with blown hot air and allowed to cool for five minutes prior to being used, to increase its flexibility. It should be utilized within ten minutes after having been dried.

FIGS. 3 and 4 show schematically the increased degree of flexibility obtained by using the high elasticity PVC or FEP barrel and soaking it in boiling water. After the barrel 60 has been soaked in boiling water, it may be easily bent from its vertical and straight position shown in FIG. 5 wherein it forms a straight line to a second position shown in FIG. 3 wherein the distal end 62 has buckled and been bent or deflected through 90°.

The force $F_1$ needed to cause this bending or deflection, shown in FIG. 3, is 0.1 ounce. Prior to placing the barrel in boiling water, the force $F_1$ is 0.2 ounce. The distal end 62 was pressed against a flat metallic surface 59. This degree of flexibility of the barrel 60 is an extremely important feature of my invention. As used herein and in the claims, the phrase "extremely flexible" and the phrase "sufficient flexibility" mean that the barrel is flexible enough to be easily bent through 90° or buckled by a force $F_1$ of 0.2 ounce or less when the distal end is pressed against a perpendicular, flat metallic surface, as shown in FIG. 3. I have found that this high degree of flexibility greatly reduces the instance of irritation and the resulting expulsion of the deposited sperm or embryo from the uterus and a failed fertilization effort. When this occurs with prior art catheters, the typical procedure is to repeat the insertion of the catheter at a later point in time which, all too frequently, causes further trauma to the walls of the cervix and uterus and repeated failure of the fertilization attempt. By using my new highly flexible and non-irritating design, I have achieved a higher fertility success rate.

FIGS. 4 and 6 show the catheter of the prior art Fischl et al U.S. Pat. No. 4,790,814. The catheter 250 has a base 251 and a barrel 260. A standard syringe 99 is shown in FIGS. 3–6 having plunger 98. Barrel 260 has a proximal end 261 and distal end 262. I have obtained a Fischl et al catheter and compared its flexibility with my invention. The force $F_2$ necessary to cause the Fischl et al catheter tip to bend through approximately 45°, as shown in FIG. 4, was 2.0 ounces. The Fischl et al catheter was held in the vertical position shown in FIG. 4 and distal end 262 was pressed against a flat metallic surface 59 to cause deflection. I attempted unsuccessfully to cause the Fischl catheter to buckle and, after applying a force of 10 ounces, the catheter simply deformed and remained deformed. As noted above, the force $F_1$ necessary to bend my catheter, as shown in FIG. 3, is only 0.1 ounce (after boiling and cool-down) or only 5% of $F_2$. Without boiling my catheter, $F_1$ is 0.2 ounce, which is only 10% of $F_2$.

Another characteristic of my new catheter is its "memory." After my catheter is held straight, as shown in FIG. 5, it can be buckled or bent through 90°, as shown in FIG. 3, released, and it will return to its straight position of FIG. 3. As noted above, the Fischl catheter would not buckle, rather it simply kinked and deformed, and remained deformed.

As shown in FIGS. 5 and 6, the length $L_1$ of my catheter is 2.1 inches, and the length $L_2$ of the Fischl et al prior art catheter is 5.7 inches. My catheter is therefore more than 60% shorter and at least ten times more flexible than the Fischl et al prior art catheter. The reduced length and increased flexibility of my catheter greatly reduce trauma to the uterine and cervical walls, increasing the likelihood of successful fertilization.

FIG. 8 is a schematic representation of the rounded hollow tip means 70 of flexible barrel means 60. In its simplest form, the rounded hollow tip means 70 is simply the distal end 62 of tube 63 which has been rounded to form a smooth, rounded surface 64 in order to minimize irritation of the cervical and uterine walls. It is to be understood that the tip means 70 could be formed of other materials and attached to the distal end of tube 63, but I have found that simply rounding the tip 62 works extremely well and avoids the necessity of connecting a tip made of some other material to the tube 63.

The catheter 50 of my invention may be utilized to introduce either semen or an embryo into the recipient's uterine cavity. When utilizing my present catheter and artificial insemination technique, it is important to introduce the semen slowly in a controlled way to produce a single drop at a time into the uterine cavity. In the preferred application, the semen is spread from the uterine cavity across the cervix and to the anterior tip of the cervix 27 in order to maximize the fertility success rate.

Figure 2:
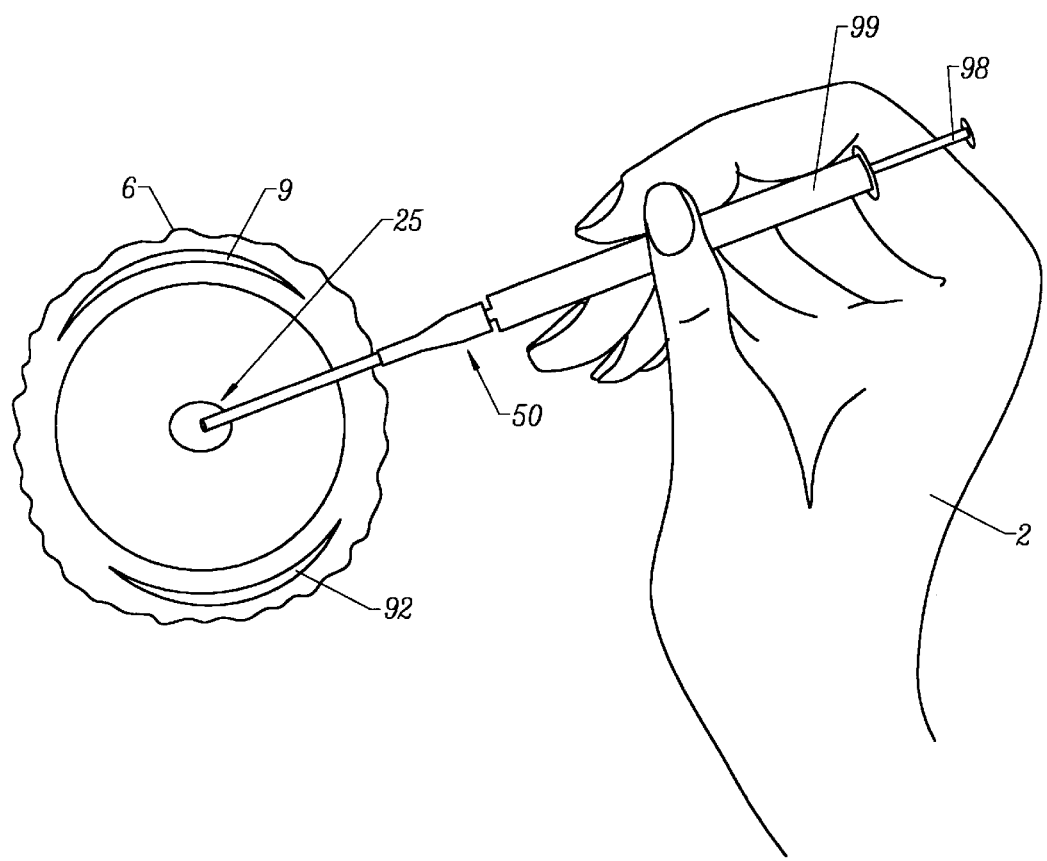
FIG. 2 is a schematic representation (intentionally not to scale) showing the catheter of the present invention as it is about to be inserted into the uterus.

FIG. 2 shows in exaggerated form the blades 91 and 92 of speculum after the vaginal walls 6 have been expanded. The cervical opening 25 is dilated and catheter 50 is being inserted into opening 25 by a clinician or doctor 2. FIG. 2 shows that my catheter is usable with little or no contact between catheter 50 and the cervical and uterine walls.

The patient is placed in Vulsalva position (in normal labor) with pelvis elevated on a firm but comfortable pillow. In this special position, all muscles, ligaments and fascia of the pelvis, abdomen and back are well relaxed. Thus, the patient is in a very comfortable position. It allows free and easy manipulation of the uterus within the pelvic cavity without resistance. The normal abdominal pressure pushes the uterus downward and at the same time the widely separated narrow blades of the speculum in the vagina allow relaxed cardinal ligaments to bring the uterus towards the vaginal interoitus and the cervix pops down into view in the speculum.

The widely separated blades of the speculum drag the anterior and posterior cervicouterine fibroblastic fascia along with underlying smooth muscles of uterus allowing uterine muscle to compress on itself (see FIG. 1), resulting in reduced total length from fundus to external cervical os and dilatation of lower uterine segment internal os and upper cervical canal. The anterior blade is the fixed blade of the speculum. Its tip can reach a higher level than the posterior blade because:

1. the anterior wall of vagina is 2 cm shorter than the posterior wall of vagina but the blades are of the same size;
2. the peritoneum and fibroelastic tissue on the anterior surface of the uterine lower segment is loose and lax and freely mobile and on the posterior surface it is closely adherent to the uterus; and
3. due to tilted pelvis in vulsalva position the distance from cervix to vaginal interoitus (external vaginal opening) is reduced, and the more oblique vaginal axis provides a clear work place; the posterior blade is the mobile blade of the speculum and allows the uterus to fall back.

All these factors together produce (as shown in FIG. 1):

1. obliteration of uterocervical angle,
2. reduced length from fundus to interoitus,
3. dilated passage from lower uterine segment internal os and upper cervical canal, and
4. fixed oblique position from fundus to interoitus with fundus at lower level than vaginal interoitus.

These factors together cause uterocervicovaginal passage to be continuously oblique, dilated, and fixed enabling sterile, quick and easy alignment of lumen of the very soft and flexible catheter.

The doctor operates from a lateral position adjacent the patient's pelvis, with the patient's pelvis approximately at waist height. This positioning maximizes visibility.

What is claimed is:

1. A method of performing either artificial insemination or embryo transplanting in female humans using a flexible catheter, while minimizing or even eliminating irritation and/or trauma of the walls of the recipient's uterus, comprising the steps:

preparing said flexible catheter for use, said catheter having a flexible, elongated barrel with a proximal and a distal end, said barrel made of either high elasticity polyvinyl chloride or fluorinated ethylene polypropylene, heating said catheter and thereafter allowing said catheter to cool, whereby said catheter becomes sufficiently flexible to buckle in response to a force of 0.1 ounce applied to said distal end, positioning the female recipient in a flat, supine position with her pelvis elevated and legs flexed, expanding the cervical canal, the internal os and the lower segment of the uterine cavity with a speculum, thereby minimizing the distance from the vaginal opening to the uterine cavity and widening the passageway through the cervical canal, the internal os and the lower segment of the uterine cavity, inserting said catheter into the recipient's vagina, through the cervical opening and into the uterine cavity within ten minutes after said catheter has cooled, and introducing either semen or an embryo through said catheter into the recipient's uterine cavity.

2. The method of claim 1 wherein the length of said catheter is 2.1 inches or less.

3. A catheter for use in either artificial insemination or in embryo transplanting in female humans, wherein the female recipient is lying flat in a supine position, with her pelvis elevated and legs flexed, comprising:

a base, and an elongated, flexible barrel having proximal and distal ends carried by said base, and wherein said elongated, flexible barrel is made of either high elasticity polyvinyl chloride or fluorinated ethylene polypropylene and is sufficiently flexible to buckle in response to a force of 0.2 ounce applied to said distal end.

4. The apparatus of claim 3 wherein said catheter is adapted to be heated and allowed to cool, and whereby said heating and cooling increases the flexibility of said elongated, flexible barrel to a point where said flexible barrel buckles in response to a force of 0.1 ounce applied to said distal end.

* * * * *

UNITED STATES PATENT AND TRADEMARK OFFICE
CERTIFICATE OF CORRECTION

PATENT NO. : 6,027,443
DATED : February 22, 2000
INVENTOR(S) : Kamala M. Nag

It is certified that error appears in the above-identified patent and that said Letters Patent is hereby corrected as shown below:

column 1, line 39,
        "tile" should be --- the ---

Signed and Sealed this

Thirtieth Day of January, 2001

Q. TODD DICKINSON

Attest:

Attesting Officer        Director of Patents and Trademarks